United States Patent

Varma

[11] Patent Number: 4,499,021
[45] Date of Patent: Feb. 12, 1985

[54] 17β(SUBSTITUTED THIO)-16-KETOANDROSTENE-17α-CARBOXYLIC ACID DERIVATIVES

[75] Inventor: Ravi K. Varma, Belle Mead, N.J.

[73] Assignee: E. R. Squibb & Sons, Inc., Princeton, N.J.

[21] Appl. No.: 599,374

[22] Filed: Apr. 12, 1984

[51] Int. Cl.³ .............................................. C07J 7/00
[52] U.S. Cl. ................................................... 260/397.1
[58] Field of Search ...................................... 260/397.1

[56] References Cited

U.S. PATENT DOCUMENTS 4,361,559 11/1982 Varma .......................... 260/397.45
4,420,428 12/1983 Varma .......................... 260/397.45

*Primary Examiner*—Elbert L. Roberts
*Attorney, Agent, or Firm*—Lawrence S. Levinson; Donald J. Barrack

[57] ABSTRACT

Topical antiinflammatory activity is exhibited by steroids having the formula

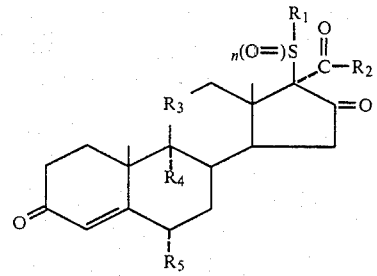

and the 1,2-dehydro derivative thereof
wherein
  $R_1$ is alkyl, cycloalkyl, aryl, alkanoyloxyalkyl or arylcarbonyloxyalkyl;
  $R_2$ is alkoxy, aryloxy, arylalkoxy, alkylthio, arylthio, or dialkylamino;
  $R_3$ is carbonyl, β-hydroxymethylene or β-acetyloxymethylene;
  $R_4$ is hydrogen or halogen;
  $R_5$ is hydrogen, methyl, hydroxy, alkanoyl, alkanoyloxy, or halogen; and
  $n$ is 0, 1 or 2.

20 Claims, No Drawings

17β(SUBSTITUTED THIO)-16-KETOANDROSTENE-17α-CARBOXYLIC ACID DERIVATIVES

BACKGROUND OF THE INVENTION

U.S. Pat. No. 4,420,428, issued Dec. 13, 1983 to Ravi K. Varma, describes steroids having topical antiinflammatory activity, and having the formula

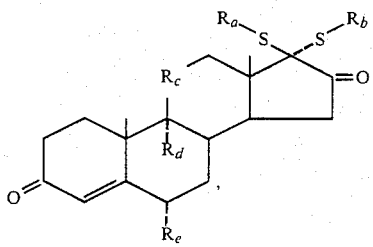

and the 1,2-dehydro and 6,7-dehydro derivatives thereof, wherein $R_a$ and $R_b$ are the same or different and each is alkyl, cycloalkyl or aryl, $R_c$ is carbonyl, β-hydroxymethylene or β-acetyloxymethylene, $R_d$ is hydrogen or halogen, and $R_e$ is hydrogen, methyl, hydroxy, alkanoyl, alkanoyloxy or halogen.

The above patent also describes intermediates having the formula

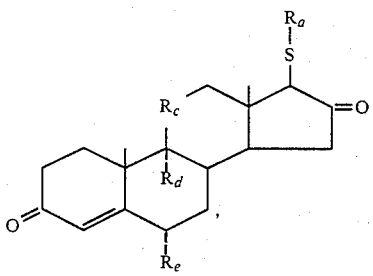

and the 1,2-dehydro derivatives thereof, wherein the symbols are as described above.

BRIEF DESCRIPTION OF THE INVENTION

Steroids having the formula

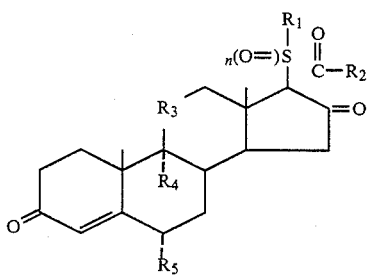

and the 1,2-dehydro derivatives thereof, have topical antiinflammatory activity. In formula I, and throughout the specification, the symbols are as defined below.

$R_1$ is alkyl, cycloalkyl, aryl, alkanoyloxyalkyl or arylcarbonyloxyalkyl;

$R_2$ is alkoxy, aryloxy, arylalkoxy, alkylthio, arylthio, or dialkylamino;

$R_3$ is carbonyl, β-hydroxymethylene or β-acetyloxymethylene;

$R_4$ is hydrogen or halogen;

$R_5$ is hydrogen, methyl, hydroxy, alkanoyl, alkanoyloxy, or halogen; and n is 0, 1 or 2.

The term "aryl", as used throughout the specification either individually or as part of a larger group, refers to phenyl or phenyl substituted with one or two alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or as part of a larger group, refer to groups having 1 to 12 carbon atoms.

The term "alkanoyl", as used throughout the specification either individually or as part of a larger group, refers to groups having 2 to 13 carbon atoms.

DETAILED DESCRIPTION OF THE INVENTION

The steroids of formula I, and the 1,2-dehydro derivatives thereof, are topical antiinflammatory agents that can be used to treat skin conditions such as dermatitis, psoriasis, sunburn, eczema, neurodermatitis, or anogenital pruritus, and in inhalation therapy for topical treatment of allergy and asthma.

For the treatment of skin conditions, the topical antiinflammatory steroids of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma, the topical antiinflammatory steroids of this invention may be administered in the conventional manner, e.g., as solid medicament which has been atomized. U.S. Pat. Nos. 3,948,264 and 4,147,166 are exemplary of the literature which describes devices that can be used to administer solid medicaments for inhalation therapy.

The steroids of formula I, and the 1,2-dehydro derivatives thereof, can be prepared from the corresponding steroids having the formula

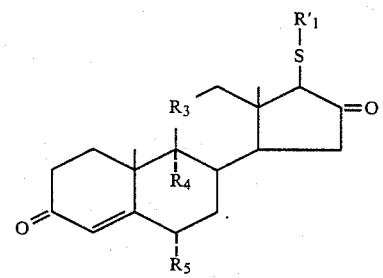

In formula II, and throughout the specification, the symbol $R'_1$ represents alkyl, cycloalkyl and aryl, and the broken line in the 1,2-position of the steroid represents the optional presence of ethylenic unsaturation.

A steroid of formula II can first be treated with a lithium dialkyl amide base (e.g., lithium diisopropyl amide) or a non-nucleophilic organic base such as 1,4-diazabicyclo[2.2.2]octane, 1,8-diazabicyclo[5.4.0]undec-7-ene, or 2,6-di(t-butyl)pyridine, to yield the corresponding 17-anion. Preferred solvents for the conversion are tetrahydrofuran, 1,2-dimethoxyethane and diethyl ether. The 17-anion can be reacted with a compound having the formula

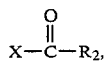

III wherein X is a halogen atom to yield the corresponding products having the formula

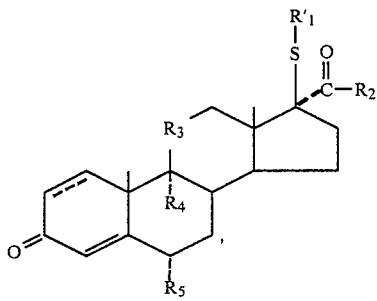

IV i.e., the products of formula I wherein n is 0 and $R_1$ is alkyl, cycloalkyl or aryl.

The products of formula I wherein $R_1$ is alkanoyloxyalkyl or arylcarbonyloxyalkyl and n is 0 can be obtained by acylation of the corresponding 17-alkylsulfoxide product (n is 1) of formula I (prepared as described below) using conventional acylation techniques.

The products of formula I wherein n is 1 or 2 can be obtained from the corresponding sulfide of formula I (i.e., n is 0) by oxidizing the sulfide with the appropriate amount of a peracid such as m-chloroperbenzoic acid or periodic acid. The use of about one equivalent of the oxidizing agent yields the sulfoxide (n is 1) and the use of excess oxidizing agent yields the sulfone (n is 2).

Alternatively, steroids of formula I wherein n is 1 or 2 can be prepared by first oxidizing a starting steroid of formula II and then adding the 17α-substituent using the procedure described above.

The starting steroids of formula II are described in U.S. Pat. No. 4,420,428, issued Dec. 13, 1983.

The following examples are specific embodiments of this invention.

EXAMPLE 1

(11β,17α)-9-Fluoro-11-hydroxy-17-(methylthio)-3,16-dioxoandrosta-1,4-diene-17-carboxylic acid, methyl ester (A)

9-Fluoro-11β-hydroxy-17α-(methylthio)androsta-3,16-dione and
9-fluoro-11β-hydroxy-17β-(methylthio)androsta-3,16-dione A solution of 905 mg (2.23 mmole) of 11β-(acetyloxy)-9-fluoro-17β-(methylthio)androsta-1,4-diene-3,16-dione in a mixture of methanol (20 ml), tetrahydrofuran (30 ml) and water (2 ml) was stirred with 3M sodium hydroxide solution (2 ml) at room temperature under nitrogen for one hour. The resulting solution was quenched with a slight excess of acetic acid. The solvent was evaporated in vacuo to give a slurry. This was diluted with water and extracted with chloroform. The chloroform solution was dried (anhydrous sodium sulfate) and evaporated in vacuo to give a mixture (0.8 g) of two isomers, which are chromatographically separable, 9-fluoro-11β-hydroxy-17α-(methylthio)androsta-3,16-dione, melting point 207°–208° C., and 9-fluoro-11β-hydroxy-17β-(methylthio)androsta-3,16-dione, melting point 228°–229° C., $[\alpha]_D^{25}$ (−)39.4° (c, 0.6; chloroform)(approximately 4:6 ratio).

(B)

(11β,17α)-9-Fluoro-11-hydroxy-17-(methylthio)-3,16-dioxoandrosta-1,4-diene-17-carboxylic acid, methyl ester To a solution of 333 mg (3.29 mmole) of diisopropylamine in 15 ml of dry tetrahydrofuran at −78° C. (acetone-Dry ice bath) was added dropwise 1.9 ml of n-butyllithium (1.7M in hexane) under nitrogen. After stirring 10 minutes at −78° C., a solution of 0.8 g (2.19 mmole) of the above mixture of 9-fluoro-11β-hydroxy-17α-(methylthio)androsta-3,16-dione and 9-fluoro-11β-hydroxy-17β-(methylthio)androsta-3,16-dione in 10 ml of dry tetrahydrofuran was added dropwise. The suspension was gradually warmed to 0° C. over the course of 1.5 hours, and then cooled to −78° C. Methyl chloroformate (1.5 ml) was added. The mixture was then warmed to 0° C., while the suspension gradually became a homogeneous solution. The resulting solution was poured into water and extracted with chloroform. The chloroform solution was dried over anhydrous sodium sulfate and evaporated in vacuo to give a gum. This was redissolved in a small amount of chloroform-hexane (4:1) and chromatographed on a 50 gram-silica gel column, eluting successively with chloroform-hexane (4:1 and 9:1), chloroform and chloroform-ethyl acetate (9:1) to give, in order of increasing polarity, the title compound (460 mg) and homogeneous 9-fluoro-11β-hydroxy-17α-(methylthio)androsta-3,16-dione (240 mg). The desired product (460 mg) was crystallized from acetone-hexane to give 400 mg of an analytical specimen, melting point 207°–208° C., $[\alpha]_D^{20}$ +48.8° (c, 0.57; chloroform) with consistent spectral data.

Anal. Calc'd. for $C_{22}H_{27}FO_5S$: C, 62.54; H, 6.44; F, 4.50; S, 7.59.

Found: C, 62.80; H, 6.52; F, 4.40; S, 7.48.

EXAMPLE 2

(11β,17α)-17-(Ethylthio)-9-fluoro-11-hydroxy-3,16-dioxoandrosta-1,4-diene-17-carboxylic acid, methyl ester To a solution of 253 mg (2.5 mmole) of diisopropylamine in 5 ml of tetrahydrofuran at −78° C. (acetone-Dry ice bath) was added dropwise 1.47 ml of n-butyllithium (1.7M in hexane) under nitrogen. After stirring 15 minutes at −78° C., a solution of 378.5 mg (1.0 mmole) of 9-fluoro-11β-hydroxy-17β-(ethylthio)androsta-3,16-dione in 3 ml of dry tetrahydrofuran was added dropwise. The suspension was gradually warmed to 0° C. in the course of 1.5 hours and then cooled to −78° C. Methyl chloroformate (0.5 ml) was then added. The mixture was warmed to 0° C., while the suspension gradually became a homogeneous solution. The resulting solution was poured into water and extracted with chloroform. The chloroform solution was dried over sodium sulfate and evaporated in vacuo to give an oil. This was combined with the product from another run (same scale) to give a total 710 mg of product. This was dissolved in chloroform and chromatographed on two precoated silica gel TLC plates (Uniplates, 20 cm×20 cm×2 mm, 1:9 ethyl acetate-chloroform for development) to give, in order of increasing polarity, 17α-

(ethylthio)-9-fluoro-11β-hydroxy-3,16-dioxoandrosta-1,4-diene-17-(methoxycarbonyl)-11-methoxycarbonate (~200 mg) and slightly impure title compound (220 mg). The desired product (220 mg) was crystallized from ethyl ether-hexane and dried to give 92 mg of a tlc-homogeneous analytical specimen, melting point 128°-130° C., $[\alpha]_D^{20}+40.0°$ (c, 0.5; chloroform) with consistent spectral data.

Anal. Calc'd. for $C_{23}H_{29}FO_5S$: C, 63.28; H, 6.70; F, 4.35; S, 7.35.

Found: C, 63.17; H, 6.68; F, 4.30; S, 7.26.

What is claimed is:

1. A steroid having the formula

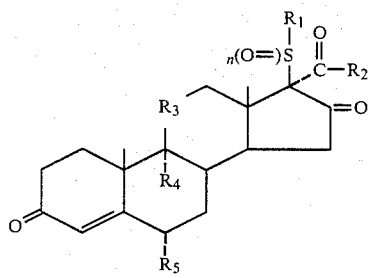

and the 1,2-dehydro derivative thereof
wherein
$R_1$ is alkyl, cycloalkyl, aryl, alkanoyloxyalkyl or arylcarbonyloxyalkyl;
$R_2$ is alkoxy, aryloxy, arylalkoxy, alkylthio, arylthio, or dialkylamino;
$R_3$ is carbonyl, β-hydroxymethylene or β-acetyloxymethylene;
$R_4$ is hydrogen or halogen;
$R_5$ is hydrogen, methyl, hydroxy, alkanoyl, alkanoyloxy, or halogen; and
n is 0, 1 or 2.

2. A steroid in accordance with claim 1 wherein $R_3$ is β-hydroxymethylene.

3. A steroid in accordance with claim 1 wherein $R_4$ is fluorine.

4. A steroid in accordance with claim 1 wherein $R_5$ is hydrogen.

5. A steroid in accordance with claim 1 wherein $R_3$ is β-hydroxymethylene, $R_4$ is fluorine and $R_5$ is hydrogen.

6. A steroid in accordance with claim 1 wherein n is 0.

7. A steroid in accordance with claim 1 wherein n is 1.

8. A steroid in accordance with claim 1 wherein n is 2.

9. A steroid in accordance with claim 5 wherein n is 0.

10. A steroid in accordance with claim 5 wherein n is 1.

11. A steroid in accordance with claim 5 wherein n is 2.

12. A steroid in accordance with claim 1 wherein $R_1$ is alkyl.

13. A steroid in accordance with claim 1 wherein $R_1$ is cycloalkyl.

14. A steroid in accordance with claim 1 wherein $R_1$ is aryl.

15. A steroid in accordance with claim 1 wherein $R_1$ is alkanoyloxyalkyl or arylcarbonyloxyalkyl.

16. A steroid in accordance with claim 1 wherein $R_2$ is alkoxy, aryloxy or arylalkoxy.

17. A steroid in accordance with claim 1 wherein $R_2$ is alkylthio or arylthio.

18. A steroid in accordance with claim 1 wherein $R_2$ is dialkylamino.

19. The steroid in accordance with claim 1, (11β,17α)-9-fluoro-11-hydroxy-17-(methylthio)-3,16-dioxoandrosta-1,4-diene-17-carboxylic acid, methyl ester.

20. The steroid in accordance with claim 1, (11β,17α)-17-(ethylthio)-9-fluoro-11-hydroxy-3,16-dioxoandrosta-1,4-diene-17-carboxylic acid, methyl ester.

* * * * *